United States Patent
Snow et al.

(10) Patent No.: US 6,554,776 B1
(45) Date of Patent: Apr. 29, 2003

(54) METHOD FOR DETECTING ANAEROBIC THRESHOLD AND PRESCRIBING A TRAINING ZONE TO MAXIMIZE FAT UTILIZATION OR IMPROVED CARDIOVASCULAR FITNESS

(75) Inventors: Michael G. Snow, White Bear Lake, MN (US); Bernhard H. Kaeferlein, Brooklyn Park, MN (US); Jeffrey G. Thieret, Shoreview, MN (US)

(73) Assignee: Medical Graphics Corporation, St. Paul, MN (US)

( * ) Notice: Subject to any disclaimer, the term of this patent is extended or adjusted under 35 U.S.C. 154(b) by 0 days.

(21) Appl. No.: 09/989,998

(22) Filed: Nov. 21, 2001

(51) Int. Cl.[7] .............................. A61B 5/08; A61B 5/02; A61B 5/00

(52) U.S. Cl. ...................... 600/532; 600/484; 600/300; 482/9

(58) Field of Search ................................. 532/508, 509, 532/526, 529, 531, 481, 483, 484, 300, 301; 482/9, 5, 900

(56) References Cited

U.S. PATENT DOCUMENTS

| | | | |
|---|---|---|---|
| 3,895,630 A | * | 7/1975 | Bachman .................... 600/531 |
| 4,463,764 A | * | 8/1984 | Anderson et al. ........... 600/532 |
| 5,297,558 A | | 3/1994 | Acorn et al. |
| 5,410,472 A | * | 4/1995 | Anderson ...................... 482/9 |
| 6,176,241 B1 | | 1/2001 | Blau et al. |
| 6,387,053 B1 | * | 5/2002 | Pessenhofer ............... 600/531 |

* cited by examiner

*Primary Examiner*—Max F. Hindenburg
*Assistant Examiner*—Navin Natnithithadha
(74) *Attorney, Agent, or Firm*—Thomas J. Nikolai; Nikolai & Mersereau, P.A.

(57) ABSTRACT

A method for prescribing an exercise regimen for a particular subject to either maximize cardiovascular performance or to lose weight involves the use of a microprocessor-based cardiopulmonary exercise system to measure oxygen uptake and carbon dioxide production on a breath-by-breath basis. These measured quantities are used to calculate energy expenditure and a subject's respiratory exchange ratio from which a fat metabolization curve can be plotted. By examining the length of a plateau in the curve where the fat substrate utilization is maximized, and noting the average heart rate in this zone, a target heart rate for optimal weight loss is arrived at. If the goal of the exercise is cardiovascular improvement, the anaerobic threshold can readily be determined as the midpoint between maximal fat utilization and the maximum acceleration towards the point where the respiratory exchange ratio becomes equal to 1 or the fat metabolism goes to 0. By noting the average heart rate at the anaerobic threshold, a target heart rate for optimizing cardiovascular fitness may be arrived at.

8 Claims, 3 Drawing Sheets

METHOD FOR DETECTING ANAEROBIC THRESHOLD AND PRESCRIBING A TRAINING ZONE TO MAXIMIZE FAT UTILIZATION OR IMPROVED CARDIOVASCULAR FITNESS

BACKGROUND OF THE INVENTION

I. Field of the Invention

This invention relates generally to a method for prescribing an exercise regimen for a particular subject, and more particularly to a method for correlating a heart rate or work rate to be maintained throughout an exercise session if the desired goal of the exercise is to reduce fat or to improve cardiovascular performance.

II. Discussion of the Prior Art

As is explained in the Acorn et al. U.S. Pat. No. 5,297, 558, which is assigned to applicant's assignee, it is well recognized that frequent exercise is beneficial to most individuals so long as it is properly engaged in, taking into account the individual's own physiologic condition. It is important that the exercise regimen not be so intensive that it adversely affects the general well being of the subject, yet not too light that it provides little or no benefit.

It is well understood that with increasing exercise, muscles need to burn metabolic fuels to perform mechanical work. Carbohydrates and fat are the typical sources of fuel and must be oxidized, using molecular $O_2$ from the atmosphere to effectively provide energy. A normal response to exercise is to increase the blood flow to the working muscles, which carries oxygen and removes carbon dioxide, the bi-product of biologic metabolism. The increasing demands for oxygenated blood are met by increasing the cardiac output (increased heart rate and increased stroke volume) and redistributing the blood flow to the working muscles and away from the abdominal area.

As a consequence of the need for more oxygen and the increased production of carbon dioxide, the level of ventilation must also increase. More air is taken in, in order to oxygenate the increased amount of blood going through the lungs and to eliminate the increased amount of carbon dioxide being brought to the lungs from the working muscles. Ventilation normally increases in direct linear fashion with $CO_2$ output rather than oxygen uptake ($VO_2$) such that the arterial carbon dioxide tension remains constant during aerobic work.

The heart rate also increases in a linear fashion with increasing $VO_2$ and the maximum heart rate is limited in any individual by age.

When the supply of oxygenated blood falls short of the oxygen needs of the muscles, anaerobic metabolism ensues. The bi-product of anaerobic metabolism is lactic acid, which is buffered by the bicarbonate system. Additional $CO_2$ is produced which must be eliminated by the lungs to keep arterial carbon dioxide tension from rising. Carbon dioxide output ($VCO_2$) will be increased relative to $VO_2$. This will be seen in graphic form as an increase in $CO_2$ output and ventilation with respect to oxygen uptake. Since the respiratory exchange ratio (RER) is the ratio of $VCO_2$ to $VO_2$, that ratio will also be seen to increase, often to values greater than 1.

The respiratory exchange ratio represents the amount of $CO_2$ produced, divided by the amount of oxygen consumed. Normally, roughly 75% of the oxygen consumed is converted to $CO_2$. Thus, RER at rest generally ranges from 0.70 to 0.85. Because RER depends on the type of fuel used by the cells, it can provide an index of carbohydrate or fat metabolism. If carbohydrates were the predominant fuel, RER would equal 1, given the following formula:

$$C_6H_{12}O_6(glucose) + 6O_2 \rightarrow 6CO_2 + H_2O$$

$$RER = VCO_2/VO_2 = 6CO_2 \div 6O_2 = 1.0$$

Because relatively more oxygen is required to burn fat, the RER for fat metabolism is lower, roughly 0.7. At high levels of exercise, $CO_2$ production exceed oxygen uptake. Thus, the RER exceeding 1.1 to 1.2 is often used to indicate the subject is giving a maximal effort. However, RER values vary greatly and generally are not a precise cut-off point for maximal exercise.

Individualized training programs must satisfy the basic goals of safety and effectiveness. Safety dictates that exercise be formed at the minimum effective heart rate whereas effectiveness dictates that the exercise program must result in the accomplishment of a desired goal, such as fat loss and improved cardiovascular fitness. In the past, many health professionals, and some exercise equipment manufacturers, use the so-called Karvonen method for determining what the heart rate should be during the exercise program if either fat burning or cardiovascular conditioning is the desired goal. In accordance with the Karvonen method, to determine the target heart rate to be maintained during a period of exercise to enhance fat burning, the following formula is commonly used:

$$\text{Target heart rate} = 220 - \text{age} - 1.6 \times \text{resting pulse rate}$$

Likewise, for cardiovascular conditioning in accordance with the Karvonen method, the following formula is utilized:

$$\text{Target heart rate} = 220 - \text{age} - 0.8 \times \text{resting pulse rate}$$

Use of the above formulas generally results in target heart rates which are too high to achieve fat reduction or higher than necessary to achieve improvements in cardiovascular fitness. Higher than necessary intensity of exercise, of course, impacts not only safety and efficacy, but also compliance. Because the high intensity of exercise results in the painful accumulation of lactate and depletion of muscle glycogen, individuals will not be able to comply with programs which specify high work intensities, such as those specified using the Karvonen predicted heart rates, and exercise will be discontinued without achieving the desired goal.

When one exercises, there are several requirements which must be met in order for the exercising muscles to perform work. At low levels of exercise, such as walking at a modest rate, the exercising muscle must have oxygen and fuel to produce energy. The two types of fuels are fats and carbohydrates. The intensity of exercise dictates which fuel will be utilized during any type of exercise. At rest, roughly equal amounts of energy are derived from carbohydrates and fats. Free fatty acids contribute greatly to energy supplied during low levels of exercise, but greater amounts of energy are derived from carbohydrates as exercise progresses. Maximal work relies virtually entirely on carbohydrates. Because endurance performance is directly related to the rate at which carbohydrates stores are depleted, two major advantages exist for both: (1) having greater glycogens stores in the muscle, and (2) deriving a relatively greater proportion of energy of from fat during prolonged exercise. Both of these benefits are conferred with training. Since carbohydrates tend to be a substantially more efficient fuel, it is the body's carbohydrates that are consumed during exercise at high levels of intensity. Fat, being a less efficient fuel, tends to be consumed by the body when exercising at relatively low levels of intensity. Therefore, if a person exercises at too high of a heart rate, fat burning objectives will not be realized.

By monitoring the Respiratory Exchange Ratio (RER), it is possible to determine which type of fuel is being utilized at any given time. It is found that the closer the RER is to 0.7, the greater the relative fat utilization. Contrariwise, the higher the intensity of exercise, the greater is the utilization of carbohydrates. By simultaneously monitoring the RER and the heart rate, it becomes possible to clearly identify the heart rate at which fat is the preferred fuel. It is commonly found that in unfit individuals, this is often at a surprisingly low level of work. In more fit individuals, fat will continue to be used as a fuel for longer periods. While exercise at an intense rate may cause a temporary weight loss due to a reduction in body water from sweating, an exercise program designed to maximize the elimination of fat should be based upon activities and exercise where the heart rate is confined to a zone corresponding to the average heart rate over an interval corresponding to a plateau of a fat metabolism curve.

Acorn et al. determined that for optimum cardiovascular improvement, exercise should be maintained in a zone such that the heart rate is maintained at the value at the anaerobic threshold plus 20%. While carbohydrates would be the fuel that is exclusively utilized at levels of exercise in this latter zone, there still exists certain benefits even for those desiring to lose fat. By improving cardiovascular fitness, the basal metabolic rate for the individual would increase. By increasing the basal metabolic rate, the number of calories that an individual routinely uses in activities of daily life increases. Interestingly, daily activities typically fall into the low intensity category in which fat is used as a fuel. So, by performing this higher intensity training on a regular basis, it is possible to improve fitness and have positive impact on fat loss.

Weight loss is achieved by sustaining a level of work for a significant duration. Maximizing fat substrate utilization is the primary goal for weight loss. Fat utilization is an aerobic process. Since exercise cannot be sustained above the anaerobic threshold, optimal fat utilization will occur before the point that anaerobic processes begin to significantly supplement energy.

During training, at work levels near the anaerobic threshold, an individual may be unable to sustain aerobic metabolism for a prolonged duration. Exercise which closely approximates the anaerobic threshold level may also be perceived as uncomfortable, which may lead premature termination of exercise. Therefore, it is important to prescribe a target heart rate that is sufficiently high to maximize fat utilization, yet far enough below the anaerobic threshold to ensure that the subject will be able to sustain the level of work. Determining the precise heart rate at which optimal fat utilization is occurring is a primary goal of the exercise prescription.

In contrast to the weight loss goal, optimal fitness training occurs above the anaerobic threshold. The goal of fitness training is to raise the anaerobic threshold level, which requires that the target heart rate be above the anaerobic threshold. Once again, a sustained work level is required and the prescription should not be so far above the anaerobic threshold that the subject prematurely terminates the exercise. The method described in the Acorn '558 patent based its prescription on an accurate determination of anaerobic threshold. Essentially, the target heart rates were determined as a fixed range below and above the anaerobic threshold. Since the target heart rates were pinned to the anaerobic threshold, if the anaerobic threshold was not measured precisely, the prescription would be less effective.

As is set out in the Blau et al. U.S. Pat. No. 6,176,241 B1, the anaerobic threshold (AT) is most commonly determined using the so-called V-Slope approach. This is the approach disclosed in the Acorn patent as well. This method is based on an analysis of the relationship between oxygen uptake ($VO_2$) and carbon dioxide output ($VCO_2$). Both $VO_2$ and $VCO_2$ increase with work. During aerobic metabolism, both values increase proportionally with a 1:1 slope. As anaerobic metabolism begins, the $VCO_2$ will begin to increase at a faster rate. The V-Slope method starts with the assumption that the metabolism was anaerobic at maximal levels. Therefore, the detection of AT is accomplished by fitting a linear regression from the maximal values backwards to the intersection with the 1:1 slope achieved during early, submaximal exercise. While the theoretical basis for this method is sound, in practice, the detection of the rate of change between two variables that are both continuing to increase during both the aerobic and the anaerobic phase can be difficult. Breath-by-breath measurements will contain a certain amount of physiologic "noise" resulting from changes in the gas concentrations of the residual volume of this reservoir of slowly ventilating air is affected by changes in the tidal breaths and respiration rate. The resulting data will fall around a median value, but will often show large swings in value with each breath. Smoothing the data through averaging produces a dampening effect that will show the AT change significantly later than the actual event.

The "V-Slope" method works best when a work rate protocol is used that delivers a smooth, small, constantly increasing workload over a short duration such as when using a bicycle ergometer. This smooth and consistent increase in workload minimizes the physiologic variability. Protocols that induce large, stepwise increases in work rate, as with treadmills, will create a resultant transitory large increase in $VO_2$ and $VCO_2$. Since this is, in fact, an increase in the rate of change, the "V-Slope" routine cannot differentiate a work rate driven change from a rate of change driven by supplemental anaerobic metabolism. Therefore, it may not be possible to accurately determine the AT. Additionally, the technique requires that the test continue until the subject has reached a maximal effort and is unable to continue. Requiring a maximal effort test on many patients is not always possible or safe.

It is accordingly a principal object of the present invention to provide a more precise, accurate target heart rate than can be realized using the anaerobic threshold determined by using the V-slope method as the basis on which the target heart rate is In the Anderson et al. U.S. Pat. No. 4,463,764, there is described a computerized exercise testing system which allows a breath-by-breath analysis of the kinetics of $O_2$ uptake, $CO_2$ output and minute ventilation on a real-time basis during exercise. Using that equipment, it is possible to compute a subject energy expenditure and the respiratory exchange ratio and, from them, to determine the range of heart rates to be maintained during exercise if fat consumption is the goal. Moreover, that same equipment may be used to determine the anaerobic threshold (AT) by locating the midpoint between maximal fat utilization and the maximal acceleration toward a RER of one in a fat metabolization curve. The heart rate in a zone beginning with the AT point and ending where RER becomes equal to 1 can be averaged and the average heart rate value used as a target heart rate for conditioning. Thus, using data derived from breath-to-breath measurements of $VO_2$ and $VCO_2$, the method to be described is able to compute the range of heart rates or work rates for enhancing fat loss and cardiopulmonary performance.

SUMMARY OF THE INVENTION

The present invention provides a method for establishing an exercise prescription for optimizing weight loss and/or cardiopulmonary fitness. It includes the steps of first providing a microprocessor-based, cardiopulmonary exercise system of a type including a respiratory flow sensor configured to sense respiratory flow of a subject while undergoing exercise at a submaximal intensity level and for measuring a resulting oxygen uptake ($VO_2$) and carbon dioxide production ($VCO_2$) on a breath-by-breath basis and a heart rate sensor for measuring the heart rate of the subject. The measured values of $VO_2$ and $VCO_2$ are used to compute energy expenditure and the respiratory exchange ratio on a breath-by-breath basis. Using those values, data representing a subject's relative fat metabolization as a function of time during an exercise period is derived. By detecting a plateau in the fat metabolization data, and by determining the subject's average heart rate at 80% of this value, the target rate for optimal weight loss is arrived at. By also observing the point of maximal fat metabolization and the point of maximum acceleration toward an RER of 1 and determining an average heart rate midway between these points, a target heart rate for optimum performance training is achieved.

DESCRIPTION OF THE PREFERRED EMBODIMENTS

Figure 1:
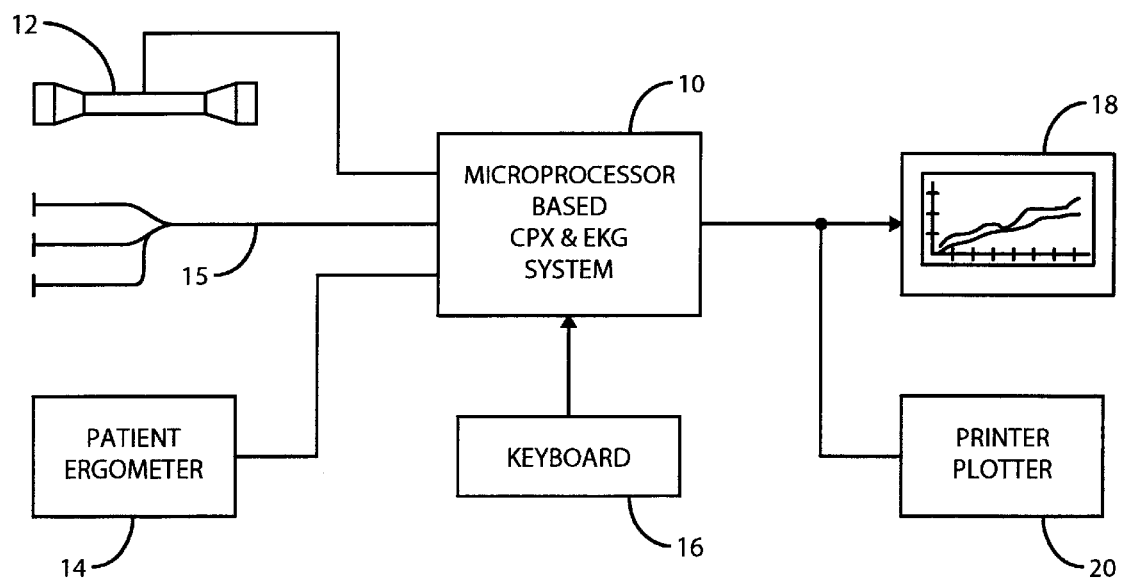
FIG. 1 is a block diagram of the equipment on which the method of the present invention is carried out.

FIG. 1 illustrates a system block diagram of the apparatus employed in carrying out the method of the present invention. It is seen to comprise a microprocessor-based cardiopulmonary exercise and heart rate monitor system 10. The system 10 is preferably of the type available from applicant's assignee, Medical Graphics Corporation, of St. Paul, Minn., and identified as its System 2000. Those seeking additional information on the construction and mode of operation of such a system may refer to the Anderson et al. U.S. Pat. No. 4,463,764, the substance of which is hereby incorporated by reference. That system, as well as more recently introduced Medical Graphics Corporation products, such as its CPX/D cardiopulmonary exercise system and its VO2000 System may be used as well. Each includes a computer and a microprocessor-based waveform analyzer and they are adapted to receive respiratory flow information, via a subject's facemask or mouthpiece pneumotach 12, work-related data, via a subject's ergometer 14, and a heart rate from a suitable heart rate monitor. The equipment 10 is able to output a variety of parameters for real-time display on a CRT device 18. Also, hard copy can be obtained via a suitable printer/plotter 20.

In use, a subject will have a heart rate monitor appropriately attached on his/her body and will have the pneumotach mouthpiece 12 positioned in the mouth as an increasing work effort is carried out on the ergometer. The ergometer may typically be a stationary bicycle, a treadmill, a stair step or other suitable device for carrying out an exercise protocol.

As the subject's exercise level increases, so, too, will heart rate and respiratory activity. The equipment shown in FIG. 1 will allow the storage and display of heart rate signals from the heart rate monitor as well as gas exchange trend graph information showing real-time, breath-by-breath data. The waveform analyzer contained within the device 10 permits oxygen and carbon dioxide gas samples to be drawn and oxygen uptake $VO_2$ and carbon dioxide output $VCO_2$ data to be computed. The manner in which the respiratory-related data and the cardiac information is processed is more particularly described in the aforereferenced Anderson et al. U.S. Pat. No. 4,463,764.

Figure 2:
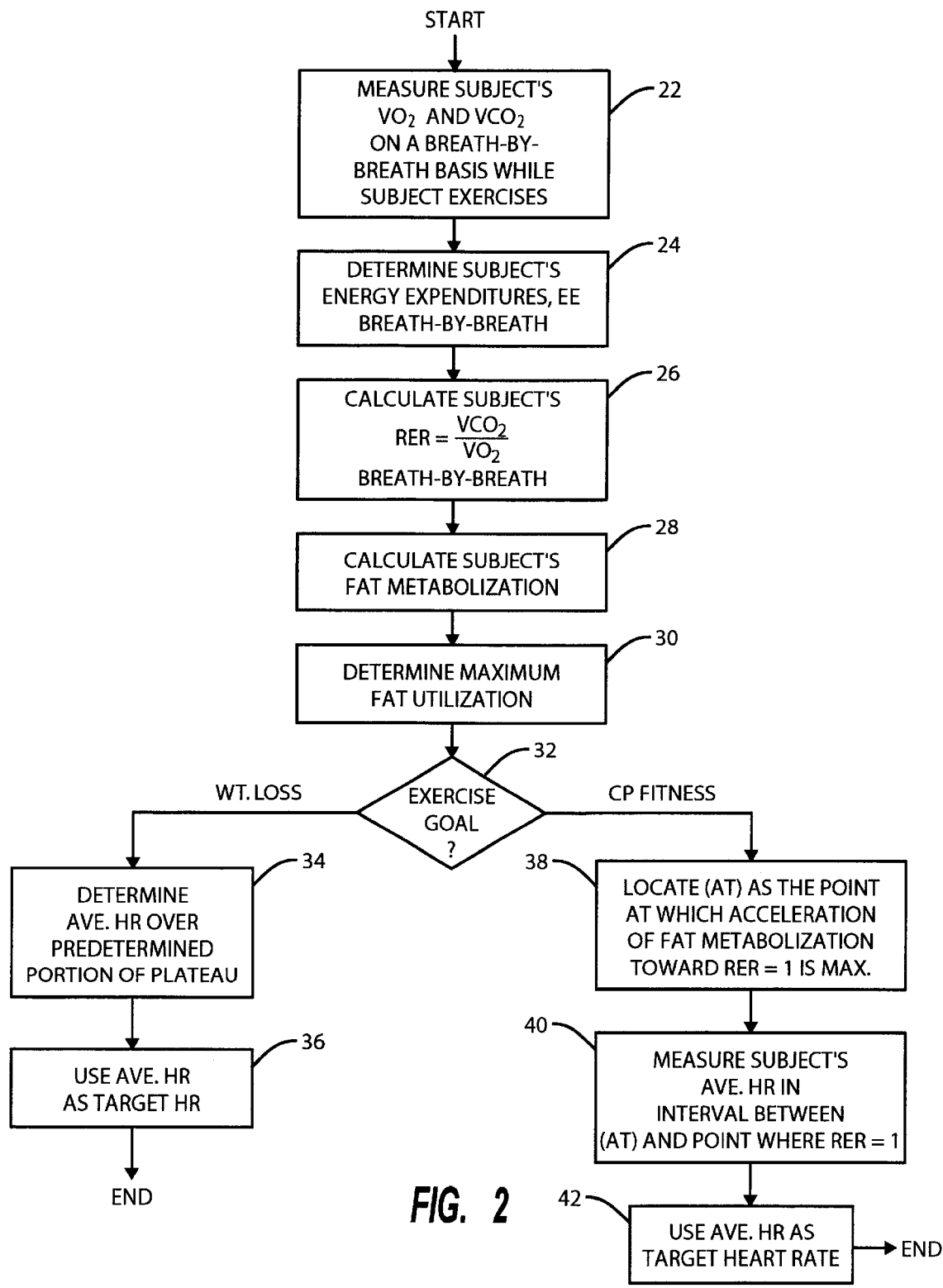
FIG. 2 is a software flow diagram for the algorithm used in arriving at an exercise prescription.

Turning next to the software flow diagram of FIG. 2, the steps employed in carrying out the method of the present invention to arrive at an appropriate exercise prescription for either optimizing weight loss or optimizing cardiopulmonary fitness will next be explained.

In carrying out the method, the subject is prepared by having a heart rate monitor affixed to his/her skin at a predetermined location on the body, the electrodes being part of the lead arrangement 15 shown in FIG. 1. The patient will also be provided with a mask that fits about the face with a minimum of dead space and which holds a mouthpiece of the pneumotach 12. As is indicated by block 22 in the flow diagram of FIG. 2, gas samples from the pneumotach are obtained whereby oxygen uptake and carbon dioxide production are measured on a breath-by-breath basis as the subject begins to perform work on a suitable ergometer.

The measured values of $VO_2$ and $VCO_2$ are used to compute the subject's energy expenditure (EE), also on a breath-by-breath basis. This may be achieved using the well-known indirect calorimetry method involving Weir's equation:

$$EE = [3.9\ (VO_2) + 1.1\ (VCO_2)]1.44$$

When $VO_2$ and $VCO_2$ are measured in units of milliliters-per-minute, EE has the units of kilocalories per 24 hours.

As is reflected by block 26, the next step in the method involves calculation of the subject's respiratory exchange ratio on a breath-by-breath basis. Following that, and as is reflected by block 28, the microprocessor is programmed to calculate the subject's fat metabolization on a breath-by-breath basis by apportioning the computed energy expenditure between carbohydrate and fat. This is accomplished by extrapolating fat utilization to be 100% at an RER of 0.7, 50% at an RER of 0.85 and 0% at an RER of 1.0. With reference to the curve of FIG. 3, at the onset of the test, because of natural anxiety and anticipation, it is quite common for a subject to hyperventilate causing initial raised or elevated RER. This may continue through early, low workload stages. However, the ventilatory demands of cellular metabolism to remove $CO_2$ rapidly becomes the controlling determinant of RER as the workload "captures" ventilatory control and overwhelms the voluntary hyperventilation.

Figure 3:
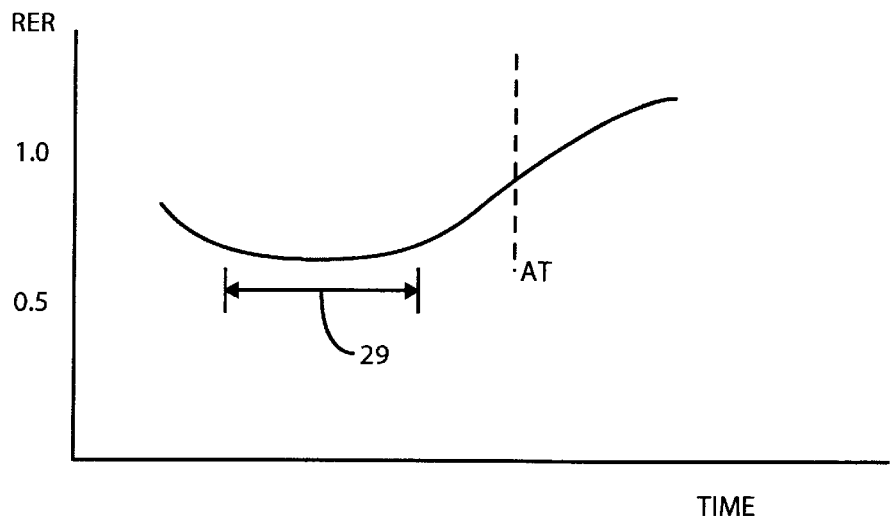
FIG. 3 is a plot of the respiratory exchange ratio (RER) vs. time during an exercise session.

In the zone labeled 29 in FIG. 3, aerobic metabolism is occurring and both oxygen uptake and carbon dioxide production are linearly related to work. Hence, as work rate increases, both $VO_2$ and $VCO_2$ increase at the same rate creating a relatively stable zone. As workload increases and carbohydrates rather than fats become a more predominant fuel, RER increases, and as the energy becomes predominantly carbohydrate based, this is refined to the anaerobic threshold, AT. At an RER of 1, all of the energy is assumed to be derived from carbohydrates.

Figure 4:
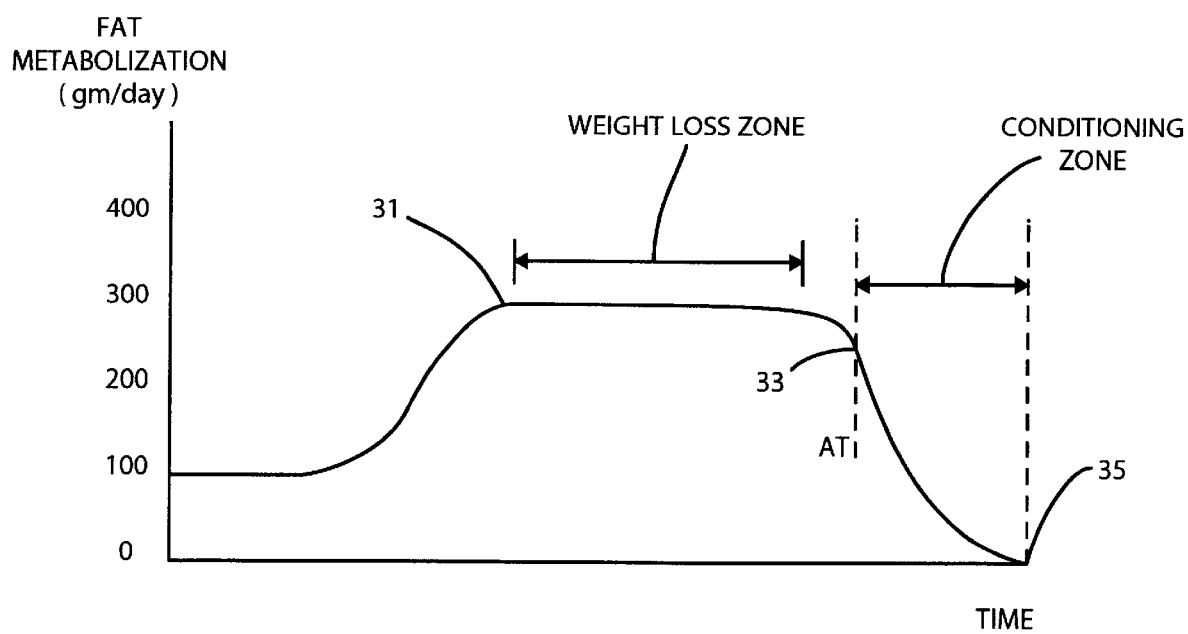
FIG. 4 is a plot of fat metabolization vs. time for that exercise session.

Referring now to FIG. 4, which shows a curve of fat metabolization vs. time, at rest and before the onset of exercise, the body's consumption of fat as a fuel is at a minimum value and relatively constant. As the exercise workload increases, the body's consumption of fat as a fuel increases reaching a plateau at point 31 where the metabolism of fat is maximized. The plateau labeled "aerobic energy" in FIG. 4 corresponds to the zone 29 in FIG. 3 where RER remains stable due to the fact that $VO_2$ and $VCO_2$ tend to increase at the same rate and are linearly related to workload. At point 33 the plateau rolls off and the point midway between maximum fat utilization and the point of maximum acceleration toward an RER of 1 is identified as the anaerobic threshold. At point 35, the point is reached where RER is equal to 1, representing the fact that it is carbohydrates that are being preferentially metabolized rather than fat.

Referring again to FIG. 2, and especially block 30, the algorithm determines the length of the plateau in fat metabolization over time. This step effectively defines the "fat zone" illustrated in FIG. 4. The curve of FIG. 4 may actually be plotted using the display 18 or the printer/plotter 20 and the point 33 located by observation. Alternatively, the software can establish the point of maximum acceleration.

At decision block 32, the goal of the exercise prescription to be developed is selected. If the goal is weight loss, the algorithm determines the average heart rate over predetermined portions of the plateau of the fat metabolization curve of FIG. 4 (block 34) and the average heart rate is then provided to the subject as the target heart rate to be used in the course of future exercise sessions. See block 36.

If, however, the goal of the exercise at the decision block 32 is cardiopulmonary fitness, then, as reflected by block 38, the next step in the algorithm is to locate the anaerobic threshold (AT) as the midpoint between maximal fat metabolization and maximum acceleration toward an RER of 1. Once the AT point has been reached anaerobic metabolism begins to contribute and the RER will once again become unstable. As is apparent in FIG. 4, the onset AT disproportionately increases $VCO_2$ resulting in a significant increase in the RER and an attendant dramatic drop in utilization of the fat substrate. It is this detection of a drop in fat utilization while $VCO_2$ is increased, that makes the present method protocol independent. Next, and reflected by block 40 in FIG. 2, the subject's average heart rate is measured in the interval between AT and the point where RER becomes equal to 1 and which is labeled by numeral 35 in FIG. 4. This average heart rate is provided to the subject as his/her target heart rate for use in future exercise sessions (block 42).

The present invention overcomes the drawbacks inherent in the use of the V-slope method for determining AT. Specifically, the present invention is not protocol-dependent. That is to say, it does not require that the work rate protocol be one that delivers a smooth, small, constantly increasing workload over a short duration as is needed when the V-slope approach is used. Secondly, the method of the present invention does not require that the exercise test continue until the subject has reached a maximum effort and is unable to continue. In the case of the present invention, the AT is detected by a readily discernible point in a fat metabolization curve where the relatively stable plateau rolls off and rapidly begins to drop to 0. Because a RER of 1.0 generally occurs significantly below maximal exercise or the onset of exercise-limiting symptoms, the method of the present invention offers an advantage over traditional testing in that it permits detection of the anaerobic threshold during a submaximal test. Moreover, since the method is insensitive to the magnitude of work rate changes, it is also insensitive to work rate protocols.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A method for establishing an exercise prescription for a patient comprising the steps of:
    (a) measuring a subject's carbon dioxide production and oxygen uptake continuously from a state of rest to a predetermined level of exercise;
    (b) calculating the subject's energy expenditure as a predetermined function of carbon dioxide production and oxygen uptake for measured values thereof;
    (c) determining the subject's respiratory exchange ratio (RER) as the ratio of carbon dioxide production to oxygen uptake continuously;
    (d) calculating data representing fat metabolization as a function of time during an exercise period;
    (e) determining the anaerobic threshold, AT, and the associate heart rate;
    (f) measuring the subject's average heart rate during a predetermined portion of time interval when the data representing fat metabolization calculated in step (d) remains relatively constant;
    (g) using the measured average heart rate computed in step (f) as a target heart rate when the goal of the exercise prescription is weight loss.

2. The method of claim 1 wherein the step of calculating the subject's energy expenditure comprises solving the equation, $EE=1.44[3.9\ (VO_2)+1.1\ (VCO_2)]$ where EE is energy expenditured measured in kilocalories/24 hours, $VO_2$ is oxygen uptake measured in milliliters/min. and $VCO_2$ is carbon dioxide output also measured in milliliters/minute.

3. The method of claim 2 wherein the step of calculating data representing fat metabolization as a function of time during an exercise period comprises apportioning EE by extrapolation from 100% fat at an RER of 0.7 to 0% fat at an RER of 1.0 where $RER=VCO_2/VO_2$.

4. The method of claim 3 and further including the step of plotting the data representing fat metabolization versus time to determine said time interval in which the fat metabolization maximizes.

5. A method for establishing an exercise prescription for a patient comprising the steps of:
    (a) measuring a subject's carbon dioxide production and oxygen uptake continuously from a state of rest to a submaximal level of exercise;
    (b) calculating the subject's energy expenditure as a predetermined function of carbon dioxide production and oxygen uptake for measured values thereof;

(c) determining the subject's respiratory exchange ratio (RER) as the ratio of carbon dioxide production to oxygen uptake continuously;

(d) calculating data representing fat metabolization as a function of time during an exercise period;

(e) determining the anaerobic threshold as the midpoint between maximum fat utilization and the point at which said data exhibits a maximum acceleration towards the point where RER=1; and (f) measuring the subject's average heart rate at the anaerobic threshold determined in step (e) and using the measured average heart rate as a target heart rate when the goal of the exercise prescription is cardiopulmonary fitness conditioning.

6. The method of claim 5 wherein the step of calculating the subject's energy expenditure comprises solving the equation, $EE=1.44[3.9\ (VO_2)+1.1\ (VCO_2)]$ where EE is energy expenditured measured in kilocalories/24 hours, $VO_2$ is oxygen uptake measured in milliliters/min. and $VCO_2$ is carbon dioxide output also measured in milliliters/minute.

7. The method of claim 6 wherein the step of calculating data representing fat metabolization as a function of time during an exercise period comprises apportioning EE by extrapolation from 100% fat utilization at an RER of 0.7 to 0% at an RER of 1.0 where $RER=VCO_2/VO_2$.

8. The method of claim 7 and further including the step of plotting the data representing fat metabolization versus time to determine the point where said data exhibits a maximum acceleration towards zero.

* * * * *